United States Patent [19]
Kim et al.

[11] Patent Number: 5,697,972
[45] Date of Patent: Dec. 16, 1997

[54] BIOPROSTHETIC HEART VALVES HAVING HIGH CALCIFICATION RESISTANCE

[75] Inventors: Young Ha Kim; Ki Dong Park; Dong Keun Han; Hack Joo Kim, all of Seoul, Rep. of Korea

[73] Assignee: Korea Institute of Science and Technology, Seoul, Rep. of Korea

[21] Appl. No.: 480,318

[22] Filed: Jun. 7, 1995

[30] Foreign Application Priority Data

Jul. 13, 1994 [KR]   Rep. of Korea ............... 9416808

[51] Int. Cl.$^6$ ............................................. A61F 2/24
[52] U.S. Cl. ..................... 623/2; 623/11; 623/901; 8/94.11; 427/2.25
[58] Field of Search ................. 623/2, 11, 901; 427/2.24, 2.25

[56] References Cited

U.S. PATENT DOCUMENTS

| | | | |
|---|---|---|---|
| 4,838,888 | 6/1989 | Nasher | 623/2 |
| 4,976,733 | 12/1990 | Girardot | 623/2 |
| 5,116,361 | 5/1992 | Kim et al. | |
| 5,182,317 | 1/1993 | Winters et al. | 604/266 |
| 5,216,087 | 6/1993 | Kim et al. | |
| 5,476,516 | 12/1995 | Seifter et al. | 623/2 |
| 5,507,804 | 4/1996 | Llanos | 623/11 |

OTHER PUBLICATIONS

In vivo "Calcification of Sulfonated PEO–grafted Biological Tissues," K.D. Park, J.Y. Yun, D.K. Han, S.Y. Jeong, K.T. Kim, H.M. Kim and Y.H. Kim, The 21st Annual Meeting of the Society for Biomaterials, Mar. 18–22, 1995, San Francisco, California, USA.

J. Biomed. Mater. Res.: Applied Biomaterials, vol. 22, pp. 11–36, 1988, F. J. Schoen, et al., "Biomaterial–Associated Calcification: Pathology, Mechanisms, and Strategies For Prevention".

Journal of Biomedical Materials Research, vol. 25, pp. 85–98, 1991, G. Golomb, et al., "Prevention of Bioprosthetic Heart Valve Tissue Calcification By Charge Modification: Effects of Protamine Binding By Formaldehyde".

The 17th Annual Meeting of the Society For Biomaterials, p. 61, May 1–5, 1991, Matthew Baldwin, et al., "FE3" Pretreatment Provides Sustained Inhibition of Bioprosthetic Heart Valve calcification".

*Primary Examiner*—Paul B. Prebilic
*Attorney, Agent, or Firm*—Oblon, Spivak, McClelland, Maier & Neustadt, P.C.

[57] ABSTRACT

The specification describes an invention of calcification resistant bioprosthetic heart valves which can be used for a long term, and have good blood compatibility and in vivo stability, and have high calcification resistance. The bioprosthetic heart valves of the invention can be prepared by binding sulfonated polyethylene oxide (PEO) derivatives covalently to the tissue. The valves have an anionic effect equal to that of chondroitin sulfate, space filling effect, and blocking effect of the carboxyl group of collagen which has been known as one factor of the calcium deposition,. In particular, the present method has better advantages in view of calcification resistance than any other conventional methods, because it suppresses thrombosis and embolism and decreases incidence of infection.

31 Claims, No Drawings

BIOPROSTHETIC HEART VALVES HAVING HIGH CALCIFICATION RESISTANCE

BACKGROUND OF THE INVENTION

1. Field of the Invention

The present invention relates to bioprosthetic heart valves having high calcification resistance and long-term durability. Specifically, the present invention relates to bioprosthetic heart valves having high calcification resistance and long-term durability, as well as good blood compatibility and in vivo stability, and a method for preparing them by binding a derivative of sulfonated polyethylene oxide covalently to the tissue.

2. Description of the Prior Art

Heart malfunction due to heart valve disorders can be treated by operating on the heart valve at a proper time. However, when the heart valve disorder is too severe to operate surgically, it may be considered to implant a prosthetic valve by means of a surgical operation. Various kinds of prosthetic valves have been developed through a replacement of materials and modification of designs over the last forty years, and mechanical valves and bioprosthetic heart valves (tissue valves) are currently in practical use.

Several kinds of mechanical valves have been studied since Starr-Edwards developed a caged ball valve and first succeeded in substitution of mitral valves (A. Starr, Ann. Surg., 154, 726, 1961). Among these, tilting disk valves and bileaflet valves are now being clinically used. These mechanical valves have a good durability, and thus maintain a uniform quality even when they are used in the body for a long time. However, they suffer from the problem that patients must take anti-coagulants in order to reduce the risk of thrombosis and embolism after implantation, and this results in hemorrhage. These valves also have many disadvantages such as the water hammer effect and poor flexibility because they are very different from normal heart valves in view of materials and hemodynamic functions. Above all, one of the important defects of the mechanical valves is hemolysis of blood sprayed out through a crack which has structurally occurred when the leaflet of valve is closed.

Carpentier firstly developed bioprosthetic heart valves in 1965 (A. Carpentier, J. Thorac. Cardiovasc. Surg., 58, 467, 1969) and now bioprosthetic heart valves derived from a porcine aortic valve or bovine pericardium which has been fixed by means of a drug treatment, are being clinically used. These valves are better than mechanical valves in many aspects that they have a shape and function similar to human heart valve and that a central blood flow can be maintained; that a pressure difference between the inlet and the outlet of the valve in the systole is lowered; that the function of the left ventricle is not disturbed; and that occurring rates of hemolysis and thrombosis are so low that there is no need to administrate an anti-coagulant for a long term. However, these bioprosthetic heart valves may have some malfunction after transplantation, such as hypertrophy shortening of the cuspid valve, rupture and centesis of the cuspid valve due to tissue degeneration and necrosis, and particularly pathological calcification.

Carpentier teaches that inflammatory reactions including immune reactions and the degeneration of collagen and elastin are the major factors of malfunction in bioprosthetic heart valves after transplantation, and suggests a new method to eliminate these factors for clinical use [A. Carpentier, Biological Tissue in Heart Valve Replacement, M. I. Ionescu et al. (Eds). Butterworth, London, 1972]. He developed a method for treating the bioprosthetic heart valve to inhibit any inflammatory reactions by host cells, to maintain or enhance its strength and flexibility under sterilized conditions, to prevent a degeneration of collagen and elastin, and to prevent the intrusion of host cells in the transplanted valve. This method comprises taking a porcine valve aseptically, washing it with Hanks solution to remove soluble antigenic material, and then oxidizing mucopolysaccharide and glycoprotein with sodium metaperiodate to form an aldehyde group on the side chains thereof. The aldehyde group thus formed may be bound with the adjacent amine group to form an intermolecular cross-linkage. The remaining sodium metaperiodate is neutralized with ethylene glycol and then residual amine groups of the glycoprotein molecule are cross-linked with glutaraldehyde buffer solution. Finally, these cross-linkages are stabilized by a reduction with sodium borohydride. However, this method has disadvantages that the durability of the transplanted valve is decreased by calcification during the long-term use.

The term "calcification" used herein means a deposition of several kinds of calcium compounds such as calcium phosphate, hydroxyapatite [$(Ca_{10}(PO_4)_6(OH)_2$] and calcium carbonate, by which the tissue material loses its physical properties, in particular flexibility due to a stress concentration, and results in flexing destruction and in vivo degradation [F. J. Schoen et al., J. Biomed. Mater. Res.: Appl. Biomat., 22(A1), 11, 1988].

To prevent such calcification from the bioprosthetic heart valves, physiologically acceptable calcification-inhibitors such as diphosphonate [R. J. Levy et al., Circulation, 71, 349, 1985], and detergents such as sodium dodecyl sulfate [R. J. Levy et al., CRC Crit. Rev. Biocompat., 2, 147, 1986] have been used for treating the tissue. Based on the fact that the calcium ions involved in the calcification are cations, a method for preventing the deposition of the calcium cation ($Ca^{++}$) by means of an electric repulsion has been studied, which comprises binding protamine to the tissue material [G. Golomb et al., J. Biomed. Mater. Res., 25, 85, 1991], or pretreating the tissue material with aluminum ions [C. L. Webb et al., TASAIO, 34, 855, 1988] or ferrous ion [M. Bailwin et al., Trans. Soc. Biomat., 14, 61, 1991] to previously introduce the cation to the tissue material.

In addition, a number of methods relating to inhibition of calcification are known in which anionic polysaccharides such as Chondroitin sulfate are introduced into the tissue [G. M. Bernacca et al., Biomaterials, 13, 345, 1992], or the tissues are treated with acetyl salicylic acid (Aspirin) (U.S. Pat. No. 4,838,888) or with aminooleic acid (WO 8906945). Other methods have also been developed based on the discovery that the cross-linking agent, glutaraldehyde per se directly affects the calcification in the bioprosthetic heart valves. It has been reported that these methods reduce the occurrence of calcification using carbodiimide, polyethylene glycol diglyceridyl ether or glycerol polyglycidylether in place of glutaraldehyde [T. Okoshi et al., TASAIO, 36, 411, 1990].

The conventional calcification inhibiting methods set forth hereinabove, can decrease the calcium deposition in the bioprosthetic heart valves to some extend, but these methods have the problems that the preparation processes are not simple, that in vivo stability and blood compatibility are not guaranteed, and that after a long-term use, mechanical properties and durability of the bioprosthetic heart valves treated as disclosed in the prior art are markedly decreased.

SUMMARY OF THE INVENTION

We, the present inventors, have intensively conducted a wide range of experiments in order to solve the problems in the prior art, and as a result, found that bioprosthetic heart valves which can be used for a long term and on which an intent of calcification may be decreased markedly can be obtained by binding an anionic hydrophilic polymer derivative of sulfonated polyethylene oxide (PEO) covalently to the tissue. Based on this, the present invention has been achieved.

It is an object of the invention to provide bioprosthetic heart valves which can be used for a long term and on which the calcification is decreased markedly.

It is another object of the invention to provide a method for preparing bioprosthetic heart valves. These and other objects of the invention can be achieved by binding an anionic hydrophilic polymer derivative of sulfonated polyethylene oxide (PEO—$SO_3$) covalently to tissue, such as porcine aortic valves and bovine pericardium.

DETAILED DESCRIPTION OF THE INVENTION

According to the modified method of the present invention, bioprosthetic heart valves having high calcification resistance, and good blood compatibility and in vivo stability can be made by binding an anionic hydrophilic polymer derivative of sulfonated polyethylene oxide (PEO—$SO_3$) covalently to the tissue (bioprosthetic tissue, BT) by means of chemically modified procedures. Further, the method of the invention provides synergistic effects. For example, an anionic effect equal to that of chondroitin sulfate, a space-filling effect, and a blocking effect of the carboxyl group of collagen which has been known as one factor to induce the calcium deposition. In particular, the method of the invention has greater advantages in view of calcification resistance than any conventional methods because it suppresses thrombosis and embolism, and decreases incidence of infection.

In accordance with the method of the invention wherein Carpentier's bioprosthetic heart valves are modified through oxidation with sodium metaperiodate, neutralization with ethylene glycol, and aldehyde activation with glutaraldehyde, thereof, the sulfonated PEO can be bound covalently to the tissue by pre- or post-treatment with glutaraldehyde. In addition, through a direct treatment of glutaraldehyde without any oxidation and neutralization of the bioprosthetic heart valves, the graft efficiency can be increased by binding the sulfonated PEO to the tissue by pre- or post-treatment with glutaraldehyde.

The tissue materials used in the present invention are a porcine aortic valve or bovine pericardium. These tissue materials are bound to the sulfonated PEO resulting in the formation of the bioprosthetic heart valves according to the invention which can be used for a long term with good calcification resistance.

The sulfonated PEO derivatives (X—PEO—$SO_3$) used in the present invention include those wherein X is an amine or an aldehyde group; $H_2N$—PEO—$SO_3$ and OHC—PEO—$SO_3$. These derivatives can be prepared by various methods. In one of the representative methods, an amine residue in the polyethylene oxide (PEO) having amine groups at both terminals is reacted with an alkyl sulfone such as propane sulfone to prepare an amine-terminated sulfonated PEO, i.e., $H_2N$—PEO—$SO_3$. This amine-terminated sulfonated PEO wherein X is an amine group is fully described in Korean Patent Application No. 93-26599 filed Dec. 6, 1993 by the inventors. The remaining unreacted amine residues of the sulfonated PEO can be also reacted with dialdehydes such as glutaraldehyde to prepare an aldehyde-terminated sulfonated PEO, i.e., OHC—PEO—$SO_3$. In this method, preferably, the PEO is a water-soluble and flexible polymeric compound. The molecular weight of the PEO is an important factor for the calcification resistance. For good calcification resistance, it is desired to use the PEO having a molecular weight of 100 to 20,000, preferably 200 to 10,000. When the molecular weight of PEO is below 100, the compound loses its inherent flexibility, and when 20,000 or more, the flexibility is decreased remarkably because the chains of the compound are so long that they may fold.

The sulfonated PEO derivatives can be added to the tissue during the oxidation of the tissue with sodium metaperiodate ($NaIO_4$), the neutralization of the tissue with ethylene glycol, or the aldehyde-activation of the tissue with glutaraldehyde. The derivatives may be also bound to the tissue using a carbodiimide such as water-soluble 1-ethyl-3-(3-dimethylaminopropyl) carbodiimide (EDC). In particular, during the EDC reaction, the pH of the aqueous solution must be acidic, and the pH of 3.0 to 5.0 is desirable.

In the present invention, glutaraldehyde is employed for fixation, storage, and aldehyde activation of the tissue. A phosphate buffered saline (PBS, pH 7.4) is used as a buffer for stabilizing the tissue, since it has stable, inert and excellent buffering ability. The amine groups of the bioprosthetic heart valve may also be blocked with a blocking agent such as acetic anhydride before the EDC reaction. When the sulfonated PEO is reacted with the tissue, the amine group in the tissue can be cross-linked to the carboxyl group of the tissue itself. This may interfere with the reaction between the sulfonated PEO (X—PEO—$SO_3$) and the carboxyl group of the tissue.

DESCRIPTION OF THE PREFERRED EMBODIMENTS

The present invention will be illustrated in greater detail by way of the following examples. The examples are presented for illustration purposes only and should not be construed as limiting the invention which is properly delineated in the claims.

EXAMPLE 1

Thirty g each of polyethylene oxide having amine groups at both terminals ($H_2N$—PEO—$NH_2$; MW 400, 1,000, 2,000, 4,000, 8,000; Nippon Oils & Fats Corp.) was added to 300 ml of tetrahydrofuran (THF) and dissolved at 50° C. for 30 minutes. Three g of propane sulfone in 15 ml of THF was added dropwise thereto and allowed to react for 5 hours. The reactants were treated with cold THF to precipitate. The mixture was filtered and then dried in vacuo at room temperature for 24 hours to give an amine-terminated sulfonated PEO; $H_2N$—PEO—$SO_3$. Then, 25 g of the sulfonated PEO was dissolved in 250 ml of distilled water, and 3 g of glutaraldehyde was added thereto. The mixture was allowed to react at 50° C. for 5 hours to give an aldehyde terminated sulfonated. PEO; OHC—PEO—$SO_3$.

Fourier transform infrared (FTIR) analysis on both $H_2N$—PEO-$SO_3$ and OHC—PEO—$SO_3$ thus prepared confirmed that characteristic peaks of –$SO_3$ and —CHO are observed at 1,030 $cm^{-1}$ and 1,730 $cm^{-1}$, respectively.

EXAMPLE 2

A bioprosthetic tissue (BT) of a porcine aortic valve was immersed in Hanks solution at 4° C. for 2 hours, and added to 200 ml of a 1% sodium metaperiodate ($NaIO_4$) solution containing a 1:1 mixture of 3% $NaIO_4$ solution and Hanks solution. The tissue was allowed to oxide at 4° C. for 24 hours in the dark. The tissue was then washed with a PBS solution, and added to 200 ml of a 1% ethylene glycol solution to neutralize at 4° C. for 1 hour. The tissue was washed again with a PBS solution, and fixed with a 0.65% glutaraldehyde solution at 4° C. for a week. The tissue thus treated was washed with a PBS solution, reduced with 0.01M sodium borohydride (NaBH$_4$) at 4° C. for 16 hours, and treated with a 4% aqueous acetic anhydride solution having pH 8 at room temperature for 3 hours to block the unreacted amine group. Then, the tissue was washed with a PBS solution, added to a 0.05M KH$_2$PO$_4$ solution containing 6.3 g of H$_2$N—PEO1000—SO$_3$. The pH of the resulting solution was adjusted to 4.4 with 1 g of EDC. The solution was allowed to react at room temperature for 24 hours, and washed with a PBS solution to prepare a modified tissue valve; BT—PEO 1000—SO$_3$.

The calcification resistance of the modified tissue thus prepared was estimated by an in vivo animal calcification test set forth below.

A male rat (80 g, 4 weeks old) was anesthetized with ketamine, and the abdominal area was shaved, cleaned with alcohol, and swabbed with iodine. Skin incision was carried out centrally at the abdominal region along the spine. Then, pouches were made in subcutaneous tissue between skin and muscle at the right and left sides, respectively, to which a modified tissue, BT—PEO—SO$_3$ (1 cm×2 cm) and a control (without PEO—SO$_3$) were transplanted at the same time and sutured. The samples (5 cases) were removed from the animal 3 weeks later, and the amount of the deposited calcium was determined by Inductivity Coupled Plasma (ICP, Plasmascan 710, Lattam Co.). The amount of calcium was expressed by the amount of deposited calcium (μg) per weight of the dried tissue (mg).

Since the tissue of the invention had much less calcium deposition (5 μg/mg) than the control (25 μg/mg), the BT—PEO1000—SO$_3$ modified according to the invention was shown to have excellent calcification resistance.

EXAMPLE 3

A bioprosthetic tissue of a bovine pericardium was immersed in 200 ml of Hanks solution (10%) containing H$_2$N—PEO400—SO$_3$ at 4° C. for 2 hours, and reacted with EDC without washing. Then, the tissue in 200 ml of a 1% H$_2$N—PEO400—SO$_3$NaIO$_4$ solution was oxidized at 4° C. for 24 hours, and neutralized at 4° C. for 1 hour in 200 ml of a 10% H$_2$N—PEO400—SO$_3$/ethylene glycol solution. The tissue thus treated was fixed with a glutaraldehyde solution at 4° C. for a week and reduced with NaBH$_4$ to prepare BT—PEO400—SO$_3$.

The calcification resistance of the modified tissue thus prepared was estimated by the in vivo calcification test described in Example 2. The results confirmed that the tissue according to the invention has excellent calcification resistance since it had much less calcium deposition (20 μg/mg) than the control (56 μg/mg).

EXAMPLE 4

A bioprosthetic tissue of a porcine aortic valve was immersed in Hanks solution at 4° C. for 2 hours, and fixed with a 0.65% glutaraldehyde solution at 4° C. for a week. The tissue was added to 200 ml of a 5% H$_2$N—PEO8000—SO$_3$ solution having pH 11, allowed to react at room temperature for 2 days, and then reduced with NaBH$_4$ to prepare BT-PEO8000-SO$_3$.

The calcification resistance of the modified tissue thus prepared was estimated by the in vivo calcification test described in Example 2. The results confirmed that the tissue according to the invention has excellent calcification resistance since it had much less calcium deposition (25 μg/mg) than the control (70 μg/mg).

EXAMPLE 5

A bioprosthetic tissue of a bovine pericardium was immersed in Hanks solution for 2 hours, and then in 50 ml of a 10% H$_2$N—PEO4000—SO$_3$ solution having pH 7.4 at room temperature for 8 hours. Fifty ml of a 2% glutaraldehyde solution was added dropwise thereto, and allowed to react at room temperature for 24 hours. The tissue was washed with a PBS solution and then further reacted with H$_2$N—PEO4000—SO$_3$ using EDC. The tissue thus treated was fixed with a glutaraldehyde solution for a week, and reduced with NaBH$_4$ to prepare H$_2$N—PEO4000—SO$_3$.

The calcification resistance of the modified tissue thus prepared was estimated by the in vivo calcification test described in Example 2. The results confirmed that the tissue according to the invention has the calcification resistance similar to that in Example 4.

EXAMPLE 6

A bioprosthetic tissue of a bovine pericardium was immersed in Hanks solution for 2 hours, and then in 50 ml of a 10% OHC—PEO1000—SO$_3$ solution having pH 7.4 at room temperature, and allowed to react at room temperature for 8 hours. The tissue was washed with a PBS solution, and further reacted with H$_2$N—PEO1000—SO$_3$ using EDC. The tissue thus treated was fixed with a glutaraldehyde solution for a week, and reduced with NaBH$_4$ to prepare BT—PEO1000—SO$_3$.

The calcification resistance of the modified tissue thus prepared was estimated by the in vivo calcification test described in Example 2. The results confirmed that the tissue according to the invention has the calcification resistance similar to that in Example 3.

EXAMPLE 7

A bioprosthetic tissue of a porcine aortic valve was immersed in Hanks solution for 2 hours, and then in 50 ml of glutaraldehyde at 4° C. for 24 hours, and washed with a PBS solution. The tissue was added to 50 ml of a 5% H$_2$N—PEO1000—SO$_3$ solution having pH 11, and allowed to react at room temperature for 24 hours. The tissue was washed with a PBS solution, and treated with an acetic anhydride solution to block the unreacted amine group. The tissue was further reacted with H$_2$N—PEO1000—SO$_3$ using EDC. The tissue thus treated was fixed with a glutaraldehyde solution for a week, and reduced with NaBH$_4$ to prepare BT—PEO1000—SO$_3$.

The calcification resistance of the modified tissue thus prepared was estimated by the in vivo calcification test described in Example 2. The results confirmed that the tissue according to the invention has excellent calcification resistance since it had much less calcium deposition (3 μg/mg) than the control (25 μg/mg).

EXAMPLE 8

A bioprosthetic tissue of a bovine pericardium was immersed in Hanks solution for 2 hours, and then in 50 ml of 2% glutaraldehyde at 4° C. for 24 hours, and washed with a PBS solution. The tissue was added to 50 ml of a 5% H$_2$N—PEO2000—SO$_3$ solution having pH 11, and the mixture allowed to react at room temperature for 24 hours.

The tissue was washed with a PBS solution, and added to 200 ml of a 1% sodium metaperiodate (NaIO$_4$) solution containing a 1:2 mixture of a 3% NaIO$_4$ solution and Hanks solution. The tissue was added to 200 ml of a 1% NaIO$_4$ solution, and oxidized at 4° C. for 24 hours in the dark. The tissue was then washed with a PBS solution, and added to 200 ml of a 1% ethylene glycol solution to neutralize at 4° C. for 1 hour. The tissue was washed with a PBS solution, and treated with an acetic anhydride solution to block the unreacted amine group. The tissue was further reacted with H$_2$N—PEO2000—SO$_3$ using EDC. The tissue thus treated was fixed with a glutaraldehyde solution for a week, and reduced with NaBH$_4$ to prepare BT—PEO2000—SO$_3$.

The calcification resistance of the modified tissue thus prepared was estimated by the in vivo calcification test described in Example 2. The results confirmed that the tissue according to the invention has the calcification resistance similar to that in Example 7.

EXAMPLE 9

A bioprosthetic tissue of a porcine aortic valve was immersed in Hanks solution for 2 hours, and then in 50 ml of 2% glutaraldehyde at 4° C. for 24 hours, and washed with a PBS solution. The tissue was added to 50 ml of a 5% H$_2$N—PEO1000—SO$_3$ solution having pH 11, and allowed to react at room temperature for 24 hours. The tissue was washed with a PBS solution, and treated with an acetic anhydride solution to block the unreacted amine group. Then, the tissue was further reacted with H$_2$N—PEO1000—SO$_3$ using EDC. The tissue was washed with a PBS solution, added to 200 ml of a 1% NaIO$_4$ solution containing a 1:2 mixture of a 3% NaIO$_4$ solution and Hanks solution. The tissue was oxidized at 4° C. for 24 hours in the dark. The tissue thus treated was washed with a PBS solution, and added to 200 ml of a 1% ethylene glycol solution to neutralize at 4° C. for 1 hours. Then, the tissue was fixed with glutaraldehyde solution for a week, and reduced with NaBH$_4$ to prepare BT—PEO1000—SO$_3$.

The calcification resistance of the modified tissue thus prepared was estimated by the in vivo calcification test described in Example 2. The results confirmed that the tissue according to the invention has the calcification resistance similar to that in Example 7.

EXAMPLE 10

BT—PEO2000—SO$_3$ was prepared as described in Example 8, except using a 1% H$_2$N—N—PEO2000—SO$_3$/NaIO$_4$ solution in place of the 1% NaIO$_4$ solution.

The calcification resistance of the modified tissue thus prepared was estimated by the in vivo calcification test as described in Example 2. The results confirmed that the tissue according to the invention has the calcification resistance similar to that in Example 7.

EXAMPLE 11

BT—PEO1000—SO$_3$ was prepared according to the same manner as described in Example 9, except using 1% H$_2$N—PEO1000—SO$_3$/NaIO$_4$ solution in place of the 1% NaIO$_4$ solution.

The calcification resistance of the modified tissue thus prepared was estimated by the in vivo calcification test described in Example 2. The results confirmed that the tissue according to the invention has the calcification resistance similar to that in Example 7.

What is claimed is:

1. A calcification resistant bioprosthetic heart valve prepared by binding an anionic hydrophilic polymer derivative of sulfonated polyethylene oxide covalently to tissue selected from the group consisting of porcine aortic valve and bovine pericardium.

2. The heart valve of claim 1, wherein the sulfonated polyethylene oxide is X—PEO—SO$_3$, wherein X is an amine or aldehyde group and PEO is polyethylene oxide, and said sulfonated polyethylene oxide is selected from the group consisting of H$_2$—N—PEO—SO$_3$ and OHC—PEO—SO$_3$.

3. The heart valve of claim 1, wherein the PEO has a molecular weight of 100 to 20,000.

4. The heart valve of claim 1, wherein the PEO has a molecular weight of 200 to 10,000.

5. The heart valve of claim 2, wherein the H$_2$N—PEO—SO$_3$ is prepared by sulfonating a terminal group of an amine terminated PEO with an alkyl sultone.

6. The heart valve of claim 5, wherein the alkyl sultone is propane sulfone.

7. The heart valve of claim 2, wherein the OHC—PEO—SO$_3$ is prepared by reacting an amine group of an amine-terminated sulfonated PEO with a dialdehyde.

8. The heart valve of claim 7, wherein the dialdehyde is glutaraldehyde.

9. The heart valve of claim 1, wherein the sulfonated PEO is added and bound to the tissue during oxidation with sodium metaperiodate, neutralization with ethylene glycol, or aldehyde activation with glutaraldehyde, thereof.

10. The heart valve of claim 1, wherein the sulfonated PEO is bound to the tissue by pre- or post-treatment of glutaraldehyde.

11. The heart valve of claim 1, wherein the sulfonated PEO is bound to the tissue using a carbodiimide.

12. The heart valve of claim 11, wherein the carbodiimide is 1-ethyl-3-(3-dimethylaminopropyl) carbodiimide.

13. The heart valve of claim 12, wherein the carbodiimide is in aqueous solution having a pH of 3.0 to 5.0.

14. The heart valve of claim 1, wherein said heart valve is in glutaraldehyde for fixation, storage and aldehyde-activation of the tissue.

15. The heart valve of claim 1, wherein said heart valve is in a phosphate buffered saline solution as a buffer for stabilizing the tissue.

16. The heart valve of claim 11, wherein amine groups on the tissue are blocked with a blocking agent before using said carbodiimide.

17. The heart valve of claim 2, wherein said tissue is a porcine aortic valve.

18. The heart valve of claim 2, wherein said tissue is a bovine pericardium.

19. A method for preparing calcification resistant bioprosthetic heart valves which comprises binding an anionic hydrophilic polymer derivative of sulfonated polyethylene oxide covalently to tissue selected from the group consisting of porcine aortic valve and bovine pericardium.

20. A method according to claim 19, wherein the sulfonated polyethylene oxide is X—PEO—SO$_3$ in which X is an amine or aldehyde group and PEO is polyethylene oxide, said sulfonated polyethylene oxide being selected from the group consisting of H$_2$N—PEO—SO$_3$ and OHC—PEO—SO$_3$.

21. A method according to claim 19, wherein the PEO has a molecular weight of 100 to 20,000.

22. A method according to claim 19, wherein the PEO has a molecular weight of 200 to 10,000.

23. A method according to claim 19, wherein said sulfonated polyethylene oxide is an amine-terminated sulfonated PEO of the formula $H_2N$—PEO—$SO_3$ prepared by sulfonating one of two terminals of amine terminated PEO with an alkyl sulfone.

24. A method according to claim 19, wherein said sulfonated polyethylene oxide is an aldehyde-terminated sulfonated PEO of the general formula OHC—PEO—$SO_3$ prepared by reacting the amine group of the amine-terminated sulfonated PEO with a dialdehyde.

25. A method according to claim 19, wherein the sulfonated PEO is added and bound to the tissue during oxidation with sodium metaperiodate, neutralization with ethylene glycol, or aldehyde activation with glutaraldehyde.

26. The method according to claim 19, wherein the sulfonated PEO is bound to the tissue by glutaraldehyde treatment.

27. The method according to claim 19, wherein the sulfonated PEO is bound to the tissue using a carbodiimide.

28. The method according to claim 27, wherein said carbodiimide is 1-ethyl-3-(3-dimethylaminopropyl) carbodiimide and said carbodiimide is in aqueous solution at a pH of 3.0 to 5.0.

29. The method according to claim 19, wherein said tissue is fixed and activated, and glutaraldehyde is used for the fixation and aldehyde-activation of the tissue.

30. The method according to claim 19, wherein a phosphate buffered saline solution is used as a buffer for stabilizing the tissue.

31. The method according to claim 26, wherein a blocking agent is used to block amine groups of the tissue prior to reacting the tissue with sulfonated PEO.

* * * * *